(12) United States Patent
Schroers et al.

(10) Patent No.: US 12,005,168 B2
(45) Date of Patent: Jun. 11, 2024

(54) APPARATUS FOR HOLDING A DISPOSABLE MEDICAL ITEM FOR TREATING BLOOD, SYSTEM AND METHOD OF OPERATION

(71) Applicant: FRESENIUS MEDICAL CARE DEUTSCHLAND GMBH, Bad Homburg (DE)

(72) Inventors: Alexander Schroers, Frankfurt (DE); Sven Marten Czerwonka, Frankfurt (DE); Robin Partenfelder, Oberursel (DE); Alexander Mosdzinski, Frankfurt (DE); Lena Maria Hahn, Bonn (DE); Jan-Willem Walde, Linden (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 826 days.

(21) Appl. No.: 17/049,345

(22) PCT Filed: Apr. 26, 2019

(86) PCT No.: PCT/EP2019/060695
§ 371 (c)(1),
(2) Date: Oct. 21, 2020

(87) PCT Pub. No.: WO2019/207082
PCT Pub. Date: Oct. 31, 2019

(65) Prior Publication Data
US 2021/0187183 A1 Jun. 24, 2021

(30) Foreign Application Priority Data
Apr. 27, 2018 (DE) ..................... 10 2018 206 633.7

(51) Int. Cl.
*A61M 1/16* (2006.01)
*A61M 1/36* (2006.01)

(52) U.S. Cl.
CPC ........ *A61M 1/1652* (2014.02); *A61M 1/3626* (2013.01); *A61M 1/363* (2014.02);
(Continued)

(58) Field of Classification Search
CPC .. A61M 1/1652; A61M 1/3626; A61M 1/363; A61M 1/3643; A61M 2205/3306;
(Continued)

(56) References Cited

U.S. PATENT DOCUMENTS 5,034,135 A * 7/1991 Fischel ................. A61M 1/262
210/651
5,770,064 A 6/1998 Jonsson et al.
(Continued)

FOREIGN PATENT DOCUMENTS

DE 102005021305 A1 11/2006

OTHER PUBLICATIONS

International Search Report and Written Opinion issued in corresponding International Patent Application No. PCT/EP2019/060695 (with English translation of International Search Report) dated Sep. 9, 2019 (23 pages).
(Continued)

*Primary Examiner* — John Kim
(74) *Attorney, Agent, or Firm* — Kilyk & Bowersox, P.L.L.C.

(57) ABSTRACT

The present invention relates to an apparatus (1) for holding a disposable medical item, in particular a dialyzer (2), plasma filter or adsorbent, for treating blood, a system (10) comprising such an apparatus, and a method for operating a disposable medical item for treating blood. A bearing device (4) is thereby configured to rotatably support the disposable item, and a drive device (5) is thereby configured to rotate the rotatably mounted disposable item around a longitudinal axis (L) extending substantially in a direction in which the
(Continued)

blood flows through the disposable item when the disposable item is in operation. Alternatively or additionally, a sensor device (6) is configured to detect a rotation of the rotatably mounted disposable item around at least one rotational axis (L, Q), in particular around the longitudinal axis (L) and/or around a transverse axis (Q) running perpendicular to the longitudinal axis (L) and output corresponding sensor data. A control device (5) is further configured to control the drive device (5) and/or process the sensor data output by the sensor device (6).

15 Claims, 1 Drawing Sheet

(52) U.S. Cl.
CPC ... *A61M 1/3643* (2013.01); *A61M 2205/3306* (2013.01); *A61M 2205/3317* (2013.01); *A61M 2205/332* (2013.01); *A61M 2205/6072* (2013.01); *A61M 2209/082* (2013.01)

(58) Field of Classification Search
CPC .... A61M 2205/3317; A61M 2205/332; A61M 2205/6072; A61M 2209/082
See application file for complete search history.

(56) References Cited

U.S. PATENT DOCUMENTS

| | | |
|---|---|---|
| 9,895,700 B2 | 2/2018 | Nguyen et al. |
| 2009/0101576 A1 | 4/2009 | Rohde et al. |
| 2012/0145615 A1 | 6/2012 | Rohde et al. |
| 2013/0112620 A1 | 5/2013 | Mueller |
| 2015/0367062 A1 | 12/2015 | Brugger et al. |

OTHER PUBLICATIONS

International Preliminary Report on Patentability issued in corresponding International Patent Application No. PCT/EP2019/060695 (English translation) dated Nov. 5, 2020 (12 pages).

Search Report issued in corresponding German Patent Application 10 2018 206 633.7 dated Dec. 11, 2018 (3 pages).

Office Action issued in corresponding European Patent Application 19 721 575.9 dated Dec. 16, 2021 (9 pages).

\* cited by examiner

APPARATUS FOR HOLDING A DISPOSABLE MEDICAL ITEM FOR TREATING BLOOD, SYSTEM AND METHOD OF OPERATION

This application is a National Stage Application of PCT/EP2019/060695, filed Apr. 26, 2019, which claims priority to German Patent Application No. 10 2018 206 633.7, filed Apr. 27, 2018.

The present invention relates to an apparatus for holding a disposable medical item for treating blood, a system comprising such an apparatus, and a method for operating a disposable medical item for treating blood.

Blood treatment apparatus having a single-use disposable item are known in the treating of a patient's blood, for instance dialysis apparatus having a dialyzer. The dialyzer has a semipermeable membrane which divides the dialyzer into two areas, whereby blood is conducted through one of the areas and a dialysate through the other of the areas so that small molecules such as for instance water, electrolytes and uremic substances from the blood can pass through the membrane into the dialysate and then be removed.

Other disposable medical items for the treatment of blood are for example plasma filters or adsorbents. Plasma filters comprise a membrane which produces a transmembrane pressure resulting in ultrafiltrate, i.e. blood plasma, being separated from the patient's blood flowing along the membrane.

An adsorbent allows pathogenic substances to be eliminated from a patient's whole blood or blood plasma. For example, adsorbents are used in so-called plasmapheresis procedures in which blood is separated into blood plasma and corpuscular components such as cells. The separated blood plasma is preferentially cleansed by way of the adsorbent and returned to the patient.

In order to simplify the operation of such disposable items, disposable items can usually be affixed to the blood treatment apparatus by means of a mounting. It can thereby be necessary or at least desirable to realign the disposable item to achieve a space-saving and less obstructive array of the tubes connecting the disposable item to the blood treatment apparatus. Moreover, re-orientating a disposable item can also be necessary or at least desirable in order to prevent or at least reduce air from being entrapped in the disposable item when the disposable item is being filled at least with blood and potentially also with another liquid such as dialysate, substituate and/or a rinsing fluid.

It is an object of the invention to improve the aligning of a disposable medical item for treating blood, in particular making it more reliable, safer and/or easier.

This object is achieved by an apparatus for holding a disposable medical item for treating blood, a system comprising such an apparatus, and a method for operating a disposable medical item for treating blood in accordance with the independent claims.

An apparatus according to the invention for holding a disposable medical item for treating blood comprises a bearing device configured to rotatably mount the disposable item, and a drive device configured to rotate the rotatably mounted disposable item around a longitudinal axis extending substantially in a direction in which the blood flows through the disposable item when the disposable item is in operation. Alternatively or additionally, the apparatus comprises a sensor device configured to detect a rotation of the rotatably mounted disposable item around at least one rotational axis, in particular around the longitudinal axis and/or around a transverse axis running perpendicular to the longitudinal axis and output corresponding sensor data. A control device is further configured to control the drive device and/or process the sensor data output by the sensor device.

A system for treating blood according to the invention comprises an inventive apparatus, a disposable item which is held by the inventive apparatus, and a blood treatment apparatus which is connected to the disposable item and configured to conduct at least blood through the disposable item for the blood treatment.

In a method according to the invention for operating a disposable item, the disposable item is rotatably mounted and rotated by a drive device around a longitudinal axis extending substantially in a direction in which blood flows through the disposable item in the operation of said disposable item and/or a rotation of the rotatably mounted disposable item around at least one rotational axis, particularly around the longitudinal axis and/or a transverse axis running perpendicular to the longitudinal axis, is detected by a sensor device and the corresponding sensor data thereby output.

One aspect of the invention is based on the approach of achieving a necessary and/or desired alignment of the disposable item by way of an automatic rotation of the disposable item around a longitudinal axis; i.e. initiated by a drive device, and/or the monitoring of the disposable item alignment, in particular the rotation of the disposable item around at least one rotational axis initiated by the drive device by means of a sensor device. This enables a precise and reliable alignment of the disposable item or its monitoring respectively and thus the reliable and smooth operation of the disposable item.

The apparatus for holding the disposable item preferably comprises a bearing device which can, for example, be designed as a gripping device and which engages at least partly around the disposable item. The bearing device preferably has an inner side facing the disposable item on which can be provided bearing elements configured for the rotatable mounting of the disposable item about the longitudinal axis. The bearing device can for example comprise at least three wheels and/or rollers in contact with the disposable item when the disposable item is being held. The disposable item can be supported so as to be rotatable about the longitudinal axis by way of the wheels, whereby at least one of the wheels and/or one of the rollers can be connected to the drive device preferably configured as an electric motor designed, for example, as a servomotor or step motor such that the rotational position of the motor shaft can be controlled and/or determined in order to effect an automatic rotation of the disposable item around the longitudinal axis.

The bearing device can thereby also comprise further bearing elements enabling the rotation of the disposable item about the transverse axis. For example, the gripping device can be rotated around the transverse axis. At least one of the further bearing elements is thereby preferably also connected to the drive device so as to effect an automatic rotation of the disposable item around the transverse axis.

The disposable item can for example thus be aligned, in particular by means of rotating about the longitudinal axis, such that tubes of a dialysis apparatus can be easily attached to the disposable item's corresponding couplers. The disposable item can then automatically be brought into a position in which the couplers and/or tubes, for example, do not obstruct a user, for instance attending personnel or a patient, whereby the risk of damage to the couplers and/or the tubes is reduced.

Alternatively or additionally, the sensor device can additionally monitor the automatic, albeit alternatively also manual, rotation of the disposable item about the longitudinal axis and/or transverse axis so as to detect misalignments, in particular when the disposable item is initially being filled with blood and/or dialysate and/or when the disposable item is being flushed with a rinsing fluid, and output if needed a corresponding notification via an output device which can be part of the apparatus for holding the disposable item or the dialysis apparatus. This can, for example, thereby prevent the inclusion of air in the disposable item upon filling and/or the pinching or at least kinking of the tube connected to the disposable item, for instance via the blood treatment apparatus.

Overall, the invention enables an improved, in particular defined, alignment of a disposable item, in particular making the alignment of the disposable item or its monitoring respectively more reliable, safer and/or easier.

In one preferential embodiment, the sensor device comprises an optical sensor configured to detect a marking located on the disposable item, in particular a barcode, during and/or subsequent to the disposable item being rotated about the at least one rotational axis and to output corresponding first sensor data. The control device is thereby preferably configured to determine information regarding the rotation and/or the rotational position of the disposable item relative to the at least one rotational axis based on the first sensor data output by the optical sensor. The alignment of the disposable item can thereby be particularly precisely and reliably determined, for example relative to the blood treatment apparatus, during or subsequent a manual or automatic rotation of the disposable item, particularly around the longitudinal axis, in particular from the couplers of the disposable item and/or associated tubes.

The optical sensor can for instance be in the form of a camera or a line sensor configured to detect a predetermined feature, e.g. a label with a barcode affixed to the disposable item or a design-related shape of the disposable item, and generate corresponding image data. The control device is thereby preferably configured to analyze the image data using an image recognition algorithm, thereby identify the feature's location on the disposable item, and from that conclude the rotation and/or rotational position.

Alternatively, the sensor device can be in the form of a magnetic sensor, for instance a coil device, and configured to detect a magnetic marking located on the disposable item during and/or subsequent the rotation of the disposable item around the at least one rotational axis and output corresponding first sensor data. This can be particularly advantageous when there is insufficient light available to operate an optical sensor.

In a further preferential embodiment, the sensor device comprises a force sensor, in particular a torque sensor, which is configured to detect a force acting on the disposable item during the rotation around the at least one rotational axis and output corresponding second sensor data. The control device is thereby preferably configured to determine an operating status of the disposable item based on the second sensor data output by the force sensor. This thereby enables a direct and reliable assessment of whether the operation of the disposable item is unimpaired, in particular without risk of damaging the disposable item.

The operating status can for example characterize the condition the disposable item is currently in and/or at which it is operated. The operating status can for instance relate to a liquid fill state of the disposable item; i.e. the operating status can for example provide information as to whether the disposable item is empty or is partly or completely filled with a fluid, in particular blood and/or e.g. a dialysate or a substituate. Alternatively or additionally, the operating status can relate to an alignment and/or position of the disposable item, in particular relative to the blood treatment apparatus; i.e. the operating status can for example provide information as to whether the disposable item is oriented vertically or horizontally or whether the disposable item, in particular couplers of the disposable item, is in contact with an obstacle.

Among other things, forces which are damaging to the disposable item can be advantageously prevented from acting on the disposable item when the disposable item is being aligned on the basis of the operating status as determined when the disposable item is for example rotated in such a manner that it comes into contact with the blood treatment apparatus.

The force sensor, for example a torque sensor, can in particular be connected to the bearing device and/or the drive device or be integrated if need be into the bearing device and/or drive device. The force sensor is preferably configured to detect resistances upon the rotation of the disposable item about at least one of the rotational axes. Thus, the second sensor data can be generated particularly reliably or the operating status respectively determined in a particularly differentiated manner.

In a further preferential embodiment, the control device is configured to determine a measure of the weight of the disposable item, in particular its empty weight, on the basis of the second sensor data output by the force sensor. Preferably, the control device is configured to determine a disposable item type, for instance its size, on the basis of the second sensor data, in particular on the basis of the measure of the empty weight, and output this information if applicable to a user. For example, the control device can determine the acceleration acting on the disposable item during a rotation of the disposable item about at least one of the rotational axes via the drive device on the basis of the second sensor data and derive a measure of the weight from same. Alternatively or additionally, the force acting on the bearing device in a predetermined rotational position of the disposable item, in which for example the longitudinal axis is horizontally aligned, can be determined from the second sensor data and the weight force or a measure of the weight of the disposable item respectively derived therefrom. It can thus be reliably verified whether the apparatus holds the appropriate disposable item for an intended treatment, for instance of a child.

If necessary, the liquid fill state in the disposable item can also be derived by the control device on the basis of the measure of the weight of the disposable item, in particular identifying a less than completely full disposable item. This thereby enables checking, in particular automatically, whether the disposable item is ready for use, e.g. completely filled with dialysate or substituate, and thus also ensures that a patient receives the proper treatment.

In one further preferential embodiment, the control device is configured to control the drive device on the basis of the sensor data output by the sensor device and/or the determined operating status and/or measure of the weight of the disposable item. This enables further increasing user comfort and/or operational reliability.

For example, upon identifying a resistance, a rotation executed via the drive device can be stopped, for instance upon assessing that the force acting on the disposable item exceeds or falls short of a predetermined force threshold. Alternatively or additionally, after the current rotational position having been identified, the disposable item can be rotated into a rotational position which is required or advantageous for a treatment step.

In a further preferential embodiment, the control device is configured to control the drive device such that the disposable item is alternatingly rotated back and forth around at least one rotational axis. Preferably, the control device is configured to control the drive device in such a manner that the rotational direction of the rotation around the at least one rotational axis changes abruptly and/or with high frequency, for instance 1 Hz or faster, preferentially 5 Hz or faster, in particular 10 Hz or faster. In particular, the control device can thereby be configured to control the drive device so as to produce a shaking motion or vibrating of the disposable item. Such shaking motion or vibrating can release air bubbles from a fluid located within the disposable item, for instance blood and/or a dialysis fluid or a substituate flowing through the disposable item.

The control device can for example be configured to trigger the forward and reverse rotation of the disposable item on the basis of an externally generated signal, for example on the basis of a detection signal automatically generated when air bubbles are detected in a fluid flowing through the disposable item. Alternatively, however, the externally generated signal can also be an input signal generated manually by a user. A user can thus manually initiate the vibrating of the disposable item, for instance after being notified that bubbles were detected or for deaeration purposes when the disposable item is being filled with a fluid. Alternatively or additionally, however, the vibration can also be executed cyclically. To that end, the control device is preferably configured to trigger the forward and reverse rotation of the disposable item via the drive device at predetermined intervals of time or as a function of the volume of blood having flown through the disposable item.

In a further preferential embodiment, the disposable medical item for treating blood is designed as a dialyzer, plasma filter or adsorbent.

In particular, the bearing device can be configured, particularly formed, such that a dialyzer, plasma filter or adsorbent is at least partially surrounded and/or can be fixed to a rotatably mounted component of the bearing device by means of a latching or clip mechanism. Dialyzer, plasma filters or adsorbents can thereby be operated in a particularly reliable manner.

In a further preferential embodiment, the disposable item exhibits a marking, in particular a barcode, whereby the marking preferably runs along a circumference of the disposable item. The sensor device, in particular an optical sensor such as for instance a camera or a magnetic sensor such as for instance a coil device, can thus easily and reliably determine a rotation and/or rotational position of the disposable item, in particular relative to the longitudinal axis.

In a further preferential embodiment, the disposable item has at least two openings through which a fluid can enter into or exit out of the disposable item during the disposable item's operation. The control device is thereby preferably configured to control the drive device such that the disposable item is rotated into a filling position in which at least one of the openings substantially lies above the liquid level of the fluid until the disposable item is completely filled with the fluid so that air can escape out of the disposable item through the at least one of the openings when the disposable item is being filled. This thereby ensures the reliable operation of the disposable item.

The fluid can in particular be a saline solution, dialysate or substituate which is conducted through the disposable item to treat a patient or for flushing purposes.

The control of the drive device by the control device can in particular be realized on the basis of a determined rotational position of the disposable item, for instance based on the sensor-detected marking on the disposable item. The disposable item can for example thereby be aligned such that the longitudinal axis is substantially perpendicular or is tilted at a predefined angle relative to a perpendicular alignment as the openings for filling the disposable item are usually situated at two opposite ends of the disposable item in the direction of the longitudinal axis. Alternatively or additionally, the control device can be configured to control the drive device such that the disposable item tilted at a predefined angle relative to a perpendicular alignment is rotated around the longitudinal axis until an opening aligned perpendicular to the longitudinal axis, for example a coupler of the disposable item for connecting to the blood treatment apparatus via a tube, is located at an upper side of the disposable item.

In a further preferential embodiment, the blood treatment apparatus comprises at least one detector configured to detect air bubbles in a fluid conducted through the disposable item prior to the fluid entering into the disposable item and/or after the fluid exiting out of the disposable item and output corresponding detector signals. The control device is thereby preferably configured to control the drive device on the basis of the detector signals such that the disposable item is alternatingly rotated back and forth around at least one rotational axis, particularly until no more air bubbles are detected. The in particular rapid and/or abrupt changing of the disposable item's rotational direction, for example at 1 Hz or faster, preferentially at 5 Hz or faster, in particular at 10 Hz or faster, can remove air bubbles from the fluid. This thereby enables safe operation of the blood treatment system.

The detector can in particular be designed as a blood leak detector for detecting blood in a fluid discharge from the disposable item, e.g. dialysate or filtrate from the dialyzer, but with the help of which air bubbles can also be detected. Alternatively or additionally, the detector can be designed as an air bubble detector for detecting air bubbles in a blood inlet and/or outlet into or out of the disposable item.

In a further preferential embodiment, the drive device rotates the disposable item at the start of operation, in particular for flushing with a rinsing fluid, into a filling position in which at least one of the at least two openings of the disposable item via which a fluid can enter into or exit out of the disposable item during the disposable item's operation is located above the liquid level of the fluid in the disposable item until the disposable item is substantially completely filled with the fluid such that air can escape out of the disposable item through the at least one of the openings when the disposable item is being filled with a fluid. Preferably, the disposable item held in the filling position is then filled with a fluid and rotated 180° about the transverse axis. This thus ensures that the disposable item's fluid completely wets the interior of the disposable item, thereby enabling e.g. particularly thorough cleansing.

When the disposable item is brought into the filling position and/or rotated about the transverse axis into an aerating position, for example by being rotated approximately 180°, the rotation or the rotational position of the disposable item respectively can be monitored by the sensor device, in particular by means of a force sensor, so that a collision of the disposable item and/or a component of the blood treatment system connected to the disposable item, for instance a coupler of the disposable item or a tube for connecting the disposable item to the blood treatment apparatus, can be immediately detected and further rotation of the disposable item prevented. This thereby enables effectively preventing damages to the disposable item and/or other components of the blood treatment system.

In a further preferential embodiment, the disposable item held in the filling position is alternatingly rotated back and forth around at least one rotational axis while being filled with the fluid. This can thereby reliably prevent or at least reduce air pockets in the disposable item.

In a further preferential embodiment, the disposable item is alternatingly rotated back and forth around at least one rotational axis at predefined intervals. The predefined intervals can for example be intervals of time or the volume of blood having flown through the disposable item such that the disposable item can be rotated back and forth at fixed intervals of time or when a specific volume of blood has been cleansed. This thereby enables a more reliable and uninterrupted operation of the disposable item.

BRIEF DESCRIPTION OF THE DRAWINGS

Further advantages, features and possible applications of the present invention are yielded by the following description in conjunction with the figures.

Shown are.

Even if the example embodiments of a system, a bearing device and a disposable item designed as a dialyzer as depicted in the figures and described below relate to applications of the invention in dialysis, the following remarks also apply to other disposable items such as plasma filters or adsorbents and corresponding systems and/or apparatus for use in other blood treatment methods.

Figure 1:
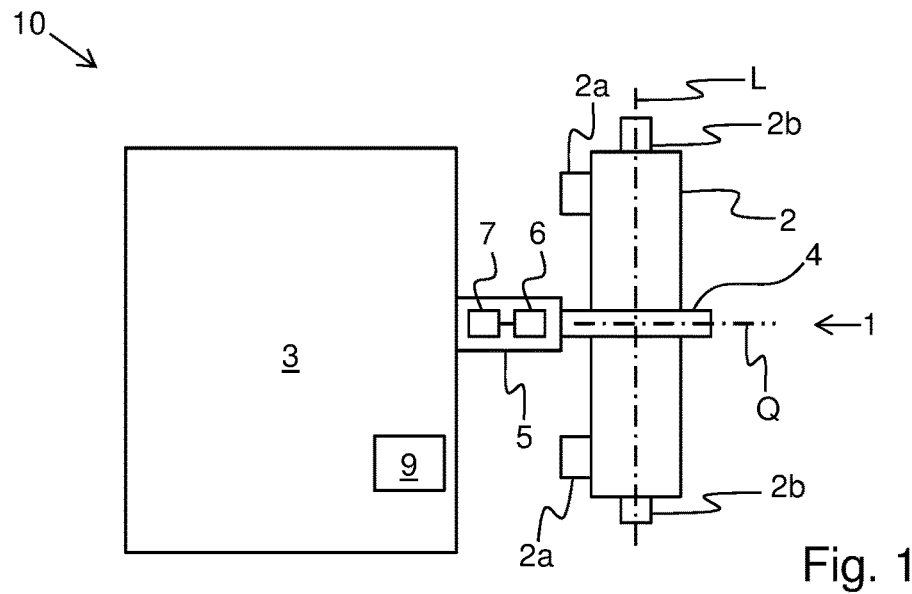
FIG. 1 one example of a system for dialysis.

FIG. 1 shows a schematic view of an example of a system 10 for dialysis having a dialyzer 2, a dialysis apparatus 3, and an apparatus 1 for holding the dialyzer 2 which is affixed to the dialysis apparatus 3. The dialysis apparatus 3 is connected to the dialyzer 2 for instance by (not shown) tubes and configured to conduct blood and dialysate through the dialyzer 2 to cleanse blood.

The dialyzer 2 is designed substantially cylindrical in the present example and has a longitudinal axis L as well as two dialysate couplers 2a and two blood couplers 2b. The dialysis apparatus 3 can conduct the blood of a patient into the dialyzer 2 or out of the dialyzer 2 via the blood couplers 2b through (not shown) tubes attached to the blood couplers by means of a (not shown) pumping device. At the same time, the dialysis apparatus 3 can conduct a dialysate for cleansing the blood guided through the dialyzer 2 through the dialyzer 2 via the dialysate couplers 2a through tubes connected to the dialysate couplers 2a by means of a (not shown) further pumping device. The blood couplers 2b are thereby arranged on two opposite ends of the dialyzer 2 in the direction of the longitudinal axis L so that the blood flows through the dialyzer 2 substantially in the direction of the longitudinal axis L during the dialyzer 2 operation, whereas the dialysate couplers 2a are arranged on the curved lateral surface of the cylindrical dialyzer 2 perpendicular to the longitudinal axis L and thus can face toward the dialysis apparatus 3 in a predetermined rotational position relative to the longitudinal axis L, as depicted in FIG. 1.

In order to, for example, be able to easily fill the dialyzer 2 with dialysate and/or blood via the respective couplers 2a, 2b prior to beginning operation or to position the dialyzer 2 in an advantageous operating position during operation in which, for example, tubes do not encumber a user of the system 100, as depicted in FIG. 1, the dialyzer 2 is rotatably supported by means of a bearing device 4. The bearing device 4 can in particular enable the aligning of the dialyzer 2 in a rotational position relative to the longitudinal axis L and/or relative to a transverse axis Q running perpendicular to the longitudinal axis L.

The apparatus 1 is additionally equipped with a drive device 5 in the present example which enables the rotatably mounted dialyzer 2 to automatically rotate around the longitudinal axis L and/or around the transverse axis Q. The drive device can, for example, comprise at least one step motor in order to precisely position the dialyzer 2 in a predetermined rotational position relative to the longitudinal and/or transverse axis L, Q, for instance in an operating position.

In order to monitor and/or control the alignment of the dialyzer 2, the apparatus 1 further comprises a control device 7 which, in addition to the drive device 5, is also connected to a sensor device 6 for detecting a rotation of the dialyzer 2 around the longitudinal and/or transverse axis L, Q. On the basis of the sensor data output by the sensor device 6, the control device 7 can for example determine a current rotational position of the dialyzer 2 relative to the longitudinal and/or transverse axis L, Q and prompt the drive device 5 to rotate the dialyzer 2 out of the current rotational position into a desired operating position. Alternatively or additionally, the control device 7 can also be configured to determine an external force acting on the dialyzer 2 on the basis of the sensor data, for instance when the rotation of the dialyzer 2 around the transverse axis Q into a filling position in which the dialyzer can be filled via the couplers 2a, 2b prior to beginning operation is obstructed by a tube, and thereupon stop the aligning of the dialyzer 2 so as to prevent damage to the dialyzer 2, in particular the couplers 2a, 2b, the tubes and/or further components of the system 10.

The control device 7 can also be configured to prompt a rotation of the dialyzer 2 around the longitudinal and/or transverse axis L, Q by means of the drive device 5 on the basis of an external signal, for example a detection signal generated by an air bubble detector 9 of the dialysis apparatus 3 or an input signal manually generated by a user. When, for instance, air bubbles are to be removed from the dialysate and/or the blood or if the user wants to prevent air bubbles from forming when filling the dialyzer 2 with blood and/or dialysate, the control device 7 can control the drive device 5 such that the dialyzer 2 is alternatingly rotated back and forth around the longitudinal axis L with high frequency, for instance 1 Hz or faster, preferably 5 Hz or faster, in particular 10 Hz or faster, and thereby vibrated.

Figure 2:
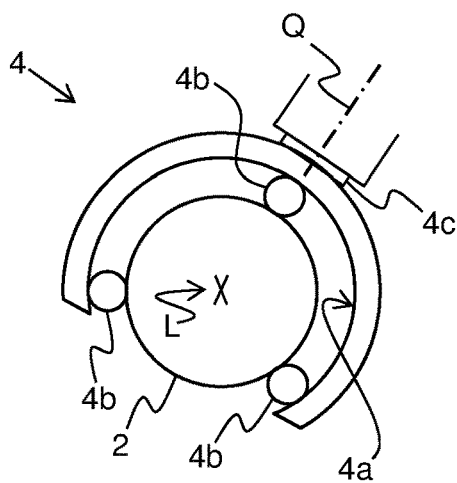
FIG. 2 one example of a bearing device.

FIG. 2 shows a cross section of one example of a bearing device 4 of an apparatus (see FIG. 1) for holding a dialyzer 2. The schematically depicted bearing device 4 is thereby designed as a gripping device and configured to at least partly engage around the cylindrically shaped dialyzer 2 in a plane perpendicular to a longitudinal axis L of the dialyzer 2. The dialyzer 2 is thereby faced toward an inner side 4a of the bearing device 4 at which three rollers 4b are arranged. The rollers 4b, which can rotate about a respective roller axis running parallel to the longitudinal axis L, contact the curved lateral surface of the dialyzer 2 such that the dialyzer 2 is rotatably supported about the longitudinal axis L.

The bearing device 4 additionally comprises a hinge 4c which allows at least one part of the bearing device 4, in particular the part of the bearing device 4 at least partly engaging around the dialyzer 2, and thus also dialyzer 2, to rotate about a transverse axis Q running perpendicular to the longitudinal axis L.

The rollers 4b and the hinge 4c can be connected to a (not shown) drive device which is configured to set the rollers 4b into rotation and thereby effect a rotation of the dialyzer 2 about the longitudinal axis L and/or actuate the hinge 4c and thereby rotate the dialyzer 2 about the transverse axis Q. In so doing, the dialyzer 2 can thus be brought automatically, in particular precisely, smoothly and reliably, into different operating positions in which the dialyzer 2 can, for example, be easily filled with a fluid, in particular dialysate, blood and/or a rinsing fluid, prior to beginning operation or so as to not encumber a user/patient during operation.

Figure 3:
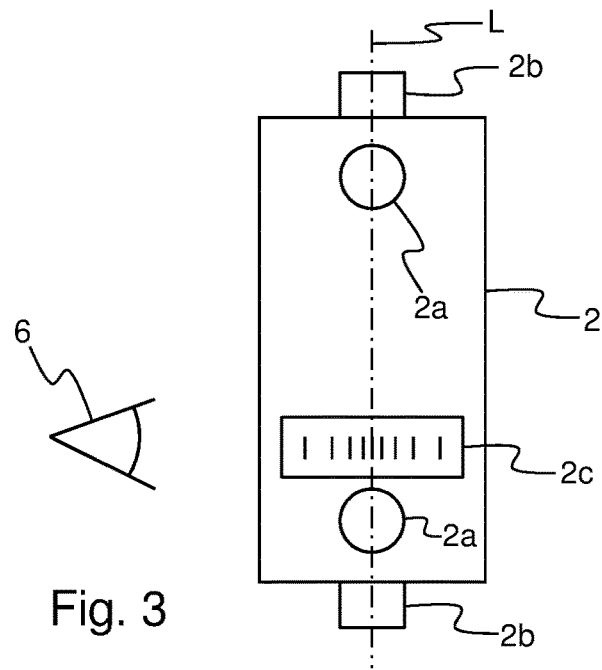
FIG. 3 one example of a dialyzer.

FIG. 3 shows a schematic depiction of one example of a dialyzer 2 which is of substantially cylindrical design and has a longitudinal axis L, multiple couplers 2a, 2b for connecting tubes via which the blood and/or dialysate can be conducted through the dialyzer 2, and a marking 2c.

The marking 2c, a barcode in the present example, is applied to the lateral surface of the dialyzer 2 and extends along the circumference of the dialyzer 2; i.e. perpendicular to the longitudinal axis L. The marking 2c is in particular positioned on the dialyzer 2 such that at least a part of the marking 2c can always be detected by a sensor device 6, for instance a camera, in a rotational position of the dialyzer 2 relative to the longitudinal axis L and corresponding sensor data can be generated. The marking 2c is thereby designed such that information on the rotational position of the dialyzer 2 relative to the longitudinal axis L can be derived from the corresponding sensor data.

For example, lines of the barcode can be at different spacings from one another depending on their position relative to dialysate couplers 2b of the dialyzer 2. By detecting the lines of the barcode facing the sensor device 6 and determining the distances of the detected lines from each other from the respective sensor data, the position of the dialysate couplers 2b relative to sensor device 6, and thus as applicable to a dialysis apparatus (see FIG. 1) with the sensor device 6 arranged at same, can consequently be concluded.

The invention claimed is:

1. An apparatus for holding a disposable medical item for treating blood comprising
   a bearing device configured to rotatably support the disposable medical item, and form a rotatably supported disposable medical item,
   a drive device configured to rotate the rotatably supported disposable medical item around a longitudinal axis extending substantially in a direction in which blood flows through the disposable medical item when the disposable medical item is in operation,
   a sensor device configured to detect a rotation of the rotatably supported disposable medical item around at least one rotational axis that is the longitudinal axis, and optionally to also detect a rotation of the rotatably supported disposable medical item around a transverse axis running perpendicular to the longitudinal axis, the sensor device being configured to output corresponding sensor data, and
   a control device configured to control the drive device and/or process the corresponding sensor data that is output by the sensor device.

2. The apparatus according to claim 1, wherein the control device is configured to control the drive device on the basis of the sensor data output by the sensor device and/or the determined operating status and/or the measure of the weight of the disposable medical item.

3. The apparatus according to claim 1, wherein the control device is configured to control the drive device such that the disposable medical item is alternatingly rotated back and forth around at least one rotational axis.

4. The apparatus according to claim 1, wherein the disposable medical item is designed as a dialyzer, plasma filter, or adsorbent.

5. A system for treating blood comprising
   the apparatus according to claim 1,
   a disposable medical item for treating blood, held by the apparatus, and
   a blood treatment apparatus connected to the disposable medical item and configured to conduct at least blood through the disposable medical item, for treating the blood.

6. The system according to claim 5, wherein the disposable medical item has a marking that is a barcode or a magnetic marking, extending along a circumference of the disposable medical item.

7. The system according to claim 5, wherein
   the disposable medical item has at least two openings through which a fluid can enter into or exit out of the disposable medical item during operation of the disposable medical item, and
   the control device is configured to control the drive device such that the disposable medical item is rotated into a filling position in which at least one of the openings substantially lies above a liquid level of the fluid until the disposable medical item is completely filled with the fluid so that air can escape out of the disposable medical item through the at least one of the openings when the disposable medical item is being filled with the fluid.

8. The system according to claim 5, wherein
   the blood treatment apparatus comprises at least one detector configured to detect air bubbles in a fluid conducted through the disposable medical item prior to the fluid entering into the disposable medical item and/or after the fluid exits out of the disposable medical item, and output corresponding detector signals, and
   the control device is configured to control the drive device based on the detector signals such that the disposable medical item is alternatingly rotated back and forth around at least one rotational axis.

9. An apparatus for holding a disposable medical item for treating blood comprising
   a bearing device configured to rotatably support the disposable medical item, and form a rotatably supported disposable medical item,
   a drive device configured to rotate the rotatably supported disposable medical item around a longitudinal axis extending substantially in a direction in which blood flows through the disposable medical item when the disposable medical item is in operation,
   a sensor device configured to detect a rotation of the rotatably supported disposable medical item around at least one rotational axis that is the longitudinal axis and/or to detect a rotation of the rotatably supported disposable medical item around a transverse axis running perpendicular to the longitudinal axis, the sensor device being configured to output corresponding sensor data, and
   a control device configured to control the drive device and/or process the corresponding sensor data that is output by the sensor device, wherein
   the sensor device comprises an optical sensor configured to detect a marking located on the disposable medical item, wherein said marking is a barcode or a magnetic marking, during and/or subsequent to the disposable medical item being rotated about the at least one rotational axis and to output corresponding first sensor data, and the control device is configured to determine information regarding a rotational position of the disposable medical item relative to the at least one rotational axis based on the first sensor data that is output by the optical sensor.

10. An apparatus for holding a disposable medical item for treating blood comprising
   a bearing device configured to rotatably support the disposable medical item, and form a rotatably supported disposable medical item,
   a drive device configured to rotate the rotatably supported disposable medical item around a longitudinal axis extending substantially in a direction in which blood flows through the disposable medical item when the disposable medical item is in operation,
   a sensor device configured to detect a rotation of the rotatably supported disposable medical item around at least one rotational axis that is the longitudinal axis, and/or to detect a rotation of the rotatably supported disposable medical item around a transverse axis running perpendicular to the longitudinal axis, the sensor device being configured to output corresponding sensor data, and
   a control device configured to control the drive device and/or process the corresponding sensor data that is output by the sensor device, wherein
   the sensor device comprises a force sensor which is configured to detect force acting on the disposable medical item during the rotation around the at least one rotational axis and output corresponding second sensor data, and
   the control device is configured to determine an operating status of the disposable medical item based on the second sensor data that is output by the force sensor.

11. The apparatus according to claim 10, wherein the control device is configured to determine a measure of the weight of the disposable medical item on the basis of the second sensor data output by the force sensor.

12. A method for operating a disposable medical item for treating blood, wherein the disposable medical item is rotatably mounted and rotated by means of a drive device around a longitudinal axis extending substantially in a direction in which blood flows through the disposable medical item, during operation of said disposable medical item, and wherein rotation of the rotatably mounted disposable medical item around at least one rotational axis that is the longitudinal axis, is detected by a sensor device, and optionally rotation of the rotatably mounted disposable medical item around a transverse axis running perpendicular to the longitudinal axis, is detected by the sensor device, and the sensor device outputs corresponding sensor data.

13. The method according to claim 12, wherein, when beginning operation, the disposable medical item
   is rotated by the drive device into a filling position in which the at least one of at least two openings of the disposable medical item, through which a fluid enters into or exits out of the disposable medical item during the operation of the disposable medical item, lies above the liquid level of the fluid in the disposal medical item until the disposable medical item is completely filled with the fluid so that air escapes out of the disposable medical item through the at least one of the openings when the disposable medical item is being filled with the fluid,
   is held in the filling position is filled with a fluid, and
   is rotated 180° about the transverse axis.

14. The method according to claim 13, wherein the disposable medical item held in the filling position is alternatingly rotated back and forth around at least one rotational axis while being filled with the fluid.

15. The method according to claim 12, wherein the disposable medical item is alternatingly rotated back and forth around at least one rotational axis at predefined intervals.

* * * * *